United States Patent
Ohkura (10) Patent No.: US 7,169,308 B2
(45) Date of Patent: Jan. 30, 2007

(54) LIQUID CHROMATOGRAPH CONTROL APPARATUS, METHOD FOR PERFORMING LIQUID CHROMATOGRAPHY AND COMPUTER PROGRAM FOR CONTROLLING A LIQUID CHROMATOGRAPH

(75) Inventor: Kihachiro Ohkura, Osaka (JP)

(73) Assignee: Yamazen Corporation (JP)

( * ) Notice: Subject to any disclaimer, the term of this patent is extended or adjusted under 35 U.S.C. 154(b) by 358 days.

(21) Appl. No.: 10/504,637

(22) PCT Filed: Feb. 14, 2003

(86) PCT No.: PCT/JP03/01522

§ 371 (c)(1),
(2), (4) Date: Aug. 12, 2004

(65) Prior Publication Data
US 2006/0231471 A1    Oct. 19, 2006

(30) Foreign Application Priority Data
Feb. 15, 2002    (JP) ............................ 2002-037722

(51) Int. Cl.
*B01D 15/08*    (2006.01)

(52) U.S. Cl. ...................... 210/656; 210/659; 210/143; 210/198.2; 436/161; 422/70; 702/30

(58) Field of Classification Search ................ 210/635, 210/656, 659, 198.2; 436/161, 518; 702/30; 422/70
See application file for complete search history.

(56) References Cited

U.S. PATENT DOCUMENTS 4,579,663 A * 4/1986 Poile et al. ................. 210/656
4,719,017 A * 1/1988 Uchino et al. .............. 210/656

(Continued)

FOREIGN PATENT DOCUMENTS

JP        2001-124755       5/2001

OTHER PUBLICATIONS

Abstract of Japan Patent 2003-240765.

*Primary Examiner*—Ernest G. Therkorn
(74) *Attorney, Agent, or Firm*—Connolly Bove Lodge & Hutz LLP (57) ABSTRACT

A liquid chromatograph control apparatus (1) includes a measured value storage (25a) that stores a measured retardation factor (Rf) value of a sample (3), which is obtained when components of the sample are separated on thin layer chromatography using eluent (4) containing a plurality of ingredients at a specified mixture ratio, in association with the specified mixture ratio, a rate-of-change-in-Rf-value storage (25b) that stores a rate of change in the Rf value of the sample (3) with respect to variation in mixture ratio of ingredients of eluent (10), a mixture ratio calculator (22a) that determines a mixture ratio of the eluent (10) at which a specified retardation factor value (RfO) of the sample is obtained, based on the measured Rf value corresponding to the specified mixture ratio stored in the measured value storage (25a) and on the rate of change in the Rf value stored in the rate-of-change-in-Rf-value storage (25b), and a mixture ratio controller (22b) that outputs a control signal to control the mixture ratio of the eluent (4) fed into a column (18) so that the Rf value of the sample (3) can be equivalent to the specified retardation factor value (RfO), based on calculated results by the mixture ratio calculator (22a).

4 Claims, 7 Drawing Sheets

U.S. PATENT DOCUMENTS

| | | | | |
|---|---|---|---|---|
| 5,203,992 A | * | 4/1993 | Drouen | 210/198.2 |
| 5,209,853 A | * | 5/1993 | Lynch et al. | 210/656 |
| 6,413,431 B1 | * | 7/2002 | Abedi | 210/656 |
| 6,524,863 B1 | * | 2/2003 | Abedi | 436/161 |
| 2002/0194898 A1 | * | 12/2002 | Klee | 73/23.35 |
| 2005/0247625 A1 | * | 11/2005 | Liu et al. | 210/635 |

* cited by examiner

LIQUID CHROMATOGRAPH CONTROL APPARATUS, METHOD FOR PERFORMING LIQUID CHROMATOGRAPHY AND COMPUTER PROGRAM FOR CONTROLLING A LIQUID CHROMATOGRAPH

REFERENCE TO RELATED APPLICATIONS

This application is a 371 of PCT/JP03/01522 filed Feb. 14, 2003.

TECHNICAL FIELD

The present invention relates to liquid chromatography using solvents (eluents) as a mobile phase and, in more detail, to establishment of conditions for liquid chromatography.

BACKGROUND ART

In liquid chromatography, a sample dissolved in eluent, mixture of solvents, as a mobile phase moves through a stationary phase packed in a column. The time for components of the sample fed into the column to flow through the column varies from one component to another, due to difference in interaction with the stationary phase and affinity for the mobile phase. As a result, components contained in the sample are separated when discharged from the column. A component having a stronger interaction with the stationary phase or a weaker affinity for the mobile phase is retained longer in the column and discharged later from the column.

Thin layer chromatography (TLC) is also taken place in the same principle as the liquid chromatography described above. In TLC, after a droplet of sample is applied to a thin-layered substance (column packing) serving as a stationary phase, the thin-layered substance is dipped in eluent serving as a mobile phase. Then, the thin-layered substance absorbs the eluent together with the sample by capillary action, allowing chromatography by this action. From the results, a retardation factor, retention factor, or rate of flow (Rf) of the sample with respect to the eluent can be determined. It is known that the Rf value thus obtained on TLC using eluent with a given solvent ratio has a correlation to resolution (Rs) value of liquid chromatography.

However, due to lack of definite indication of the correlation between the Rf value and the Rs value, results on TLC are not applied to liquid chromatography. Accordingly, in the existing circumstances, for liquid chromatography to be performed at a better Rs value, following steps are taken. Liquid chromatography is performed at an arbitrary Rf value, first. Then, based on the obtained results, an optimum Rs value is sought by changing conditions such as the ratio between polar solvent and non-polar solvent contained in eluent. If a Rf value obtained is, for example, higher than a preset Rf value, then liquid chromatography must be performed again by reducing the proportion of polar solvent to eluent. Thus, it is necessary that liquid chromatography is performed repeatedly with changes by changing the ratio between polar solvent and non-polar solvent until an optimum Rf value for separation of components is sought out. This involves troublesome and time-consuming works and also requires a large amount of eluent.

In the light of the disadvantages mentioned above, the present invention has been made. It is an object of the present invention to provide a liquid chromatograph control apparatus by which chromatography can be performed under such a condition of eluent as an optimum Rf value is obtained without troublesome works, a method for performing liquid chromatography, and a computer program for controlling a liquid chromatograph.

DISCLOSURE OF THE INVENTION

After having devoted himself to study on the means for solving the problems mentioned above, the inventor has obtained the knowledge that there is a proportionality relation between a mixture ratio of ingredients of eluent and a Rf value of a sample and that a rate of change in the Rf value of a sample with respect to the mixture ratio of ingredients of eluent is fixed even for different kinds of samples.

The present invention has been made based on this knowledge. The present invention provides a liquid chromatograph control apparatus comprising measured value storage that stores a measured retardation factor (Rf) value of a sample, which is obtained when components of the sample are separated on thin layer chromatography using eluent containing a plurality of ingredients at a specified mixture ratio, in association with the specified mixture ratio, rate-of-change-in-Rf-value storage that stores a rate of change in the retardation factor (Rf) value of the sample with respect to variation in mixture ratio of ingredients of eluent, mixture ratio calculator that determines a mixture ratio of the eluent at which a specified retardation factor value (RfO) of the sample is obtained, based on the measured retardation factor (Rf) value corresponding to the specified mixture ratio stored in the measured value storage and on the rate of change in the retardation factor (Rf) value stored in the rate-of-change-in-Rf-value storage, and mixture ratio controller that outputs a control signal to control the mixture ratio of the eluent fed into a column so that the retardation factor (Rf) value of the sample can be equivalent to the specified retardation factor value (RfO), based on calculated results by the mixture ratio calculator.

Also, the present invention provides a method for performing liquid chromatography comprising a first step for obtaining a measured retardation factor (Rf) value of a sample by performing thin layer chromatography using eluent containing a plurality of ingredients at a specified mixture ratio, a second step for determining a mixture ratio of the eluent at which a specified retardation factor value (RfO) is obtained, by using a rate of change in the retardation factor (Rf) value of the sample with respect to variation in mixture ratio of ingredients of eluent, based on the measured retardation factor (Rf) value obtained in the first step and on the specified mixture ratio of the eluent at which the measured retardation factor (Rf) value is obtained, and a third step for feeding into a column the eluent having the mixture ratio determined in the second step at which the specified retardation factor value (RfO) is obtained.

The structure mentioned above can provide the result that a mixture ratio of eluent for a desired specified retardation factor value (RfO) of a sample can be obtained by simply determining a Rf value of the sample for any specific mixture ratio of eluent on TLC. This enables chromatography to be performed under such a condition of eluent as an optimum retardation factor value (RfO) is obtained without troublesome works.

In the liquid chromatograph control apparatus of the invention, the rate-of-change-in-Rf-value storage may store the rate of change in the Rf value of the sample with respect to variation in mixture ratio of ingredients of eluent for respective types of eluent different in combination of ingredients.

This structure can provide the advantage of enabling the liquid chromatograph control apparatus to be applied to various types of eluent different in combination of ingredients.

According to another aspect of the present invention, there is provided a computer program for controlling a liquid chromatograph, wherein the program causes a computer to function as the above-described liquid chromatograph control apparatus. This program can be distributed by recording it in removable recording media such as a CD-ROM (compact disk read-only memory) disk, a FD (flexible disk), and a MO (magnetooptic disk), as well as by means of communication network such as Internet through wired or wireless electrical communication means.

BEST MODE FOR CARRYING OUT THE INVENTION

In the following, certain preferred embodiments of the present invention will be described with reference to FIGS. 1 through 7.

Figure 1:
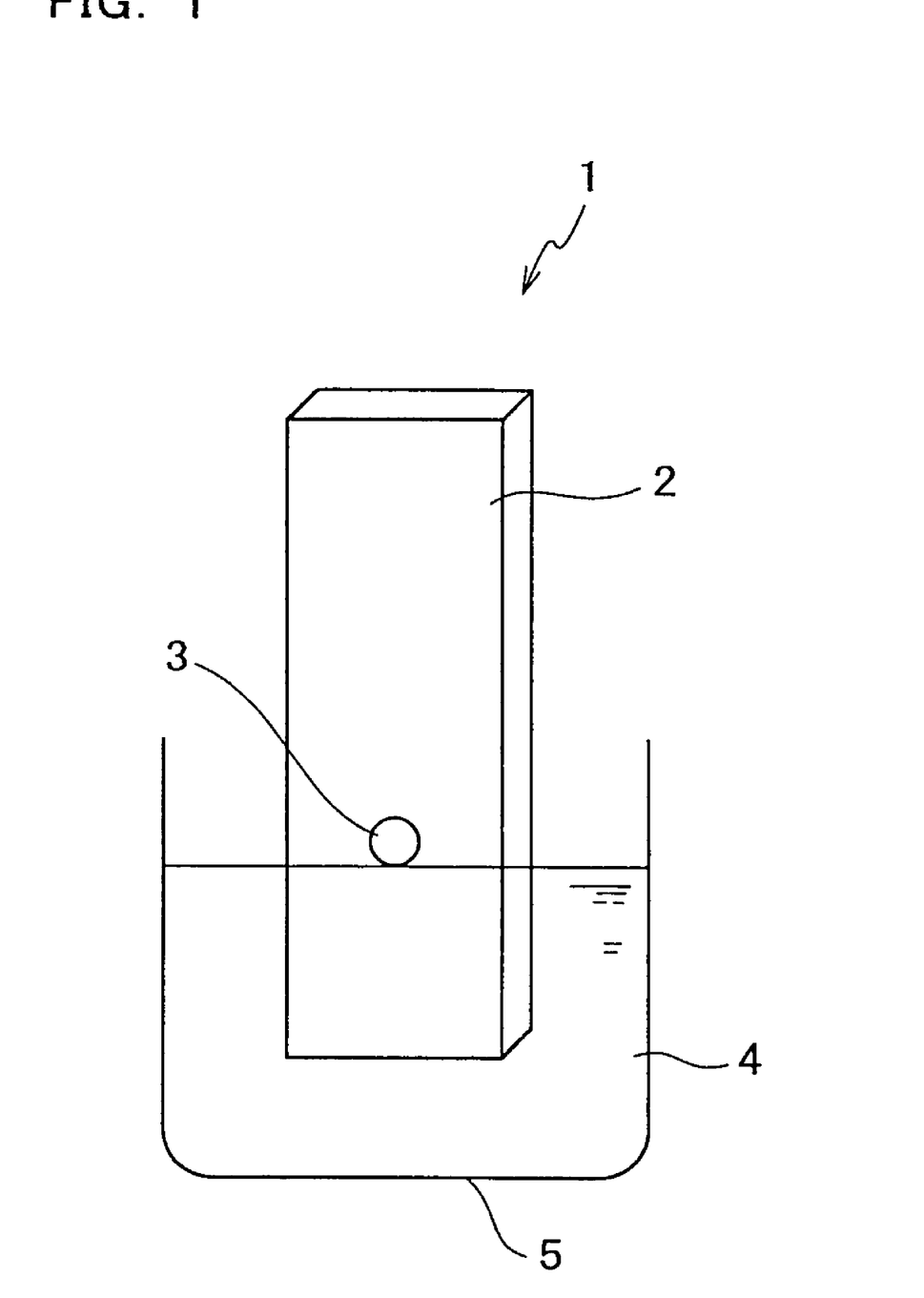
FIG. 1 is a perspective view showing an apparatus used for TLC.
Figure 2:
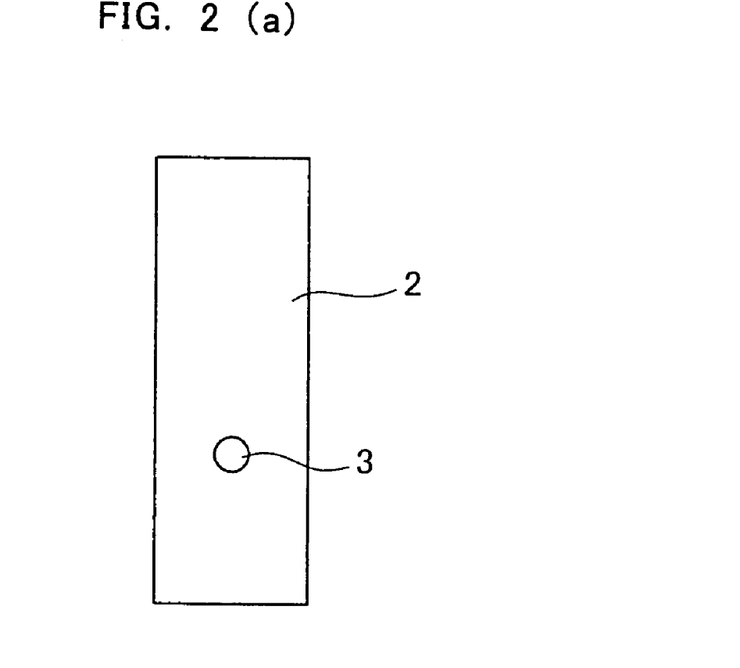
FIG. 2 is a schematic diagram of a silica gel thin-layered plate used for TLC: (a) and (b) showing Before TLC and After TLC, respectively.

Shown in FIG. 1 is an apparatus 1 used for thin layer chromatography (TLC). The TLC apparatus 1 comprises a silica-gel thin-layered plate 2 on which a droplet of sample 3 is spotted, and eluent 4 stored in a reservoir 5. The sample 3, silica gel forming the silica-gel thin-layered plate 2, and the eluent 4 are the same as those used in liquid chromatography mentioned later.

Figure 3:
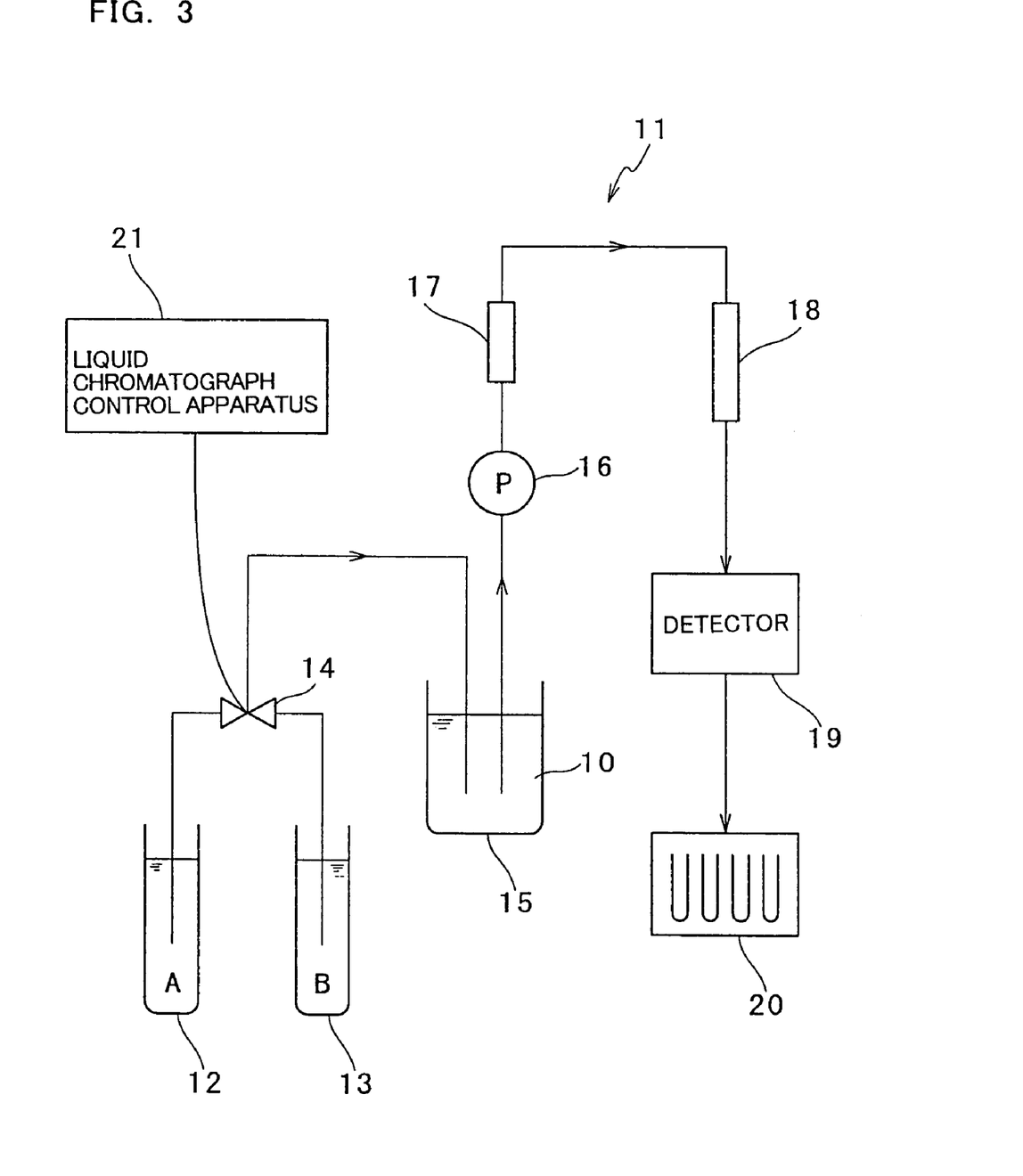
FIG. 3 is a schematic diagram showing a liquid chromatograph to which the present invention is applied.

Shown in FIG. 3 is a liquid chromatograph 11. The liquid chromatograph 11 comprises a reservoir 12 in which a solvent A is reserved, a reservoir 13 in which a solvent B is reserved, a solenoid valve 14 disposed at a location where the solvents A and B are connected to each other, a mixer 15 for reserving eluent 10, a pump 16, an injector 17, a column 18, a detector 19, and a fraction collector 20, which are arranged in this order, to form a route line. A liquid chromatograph control apparatus 21 is connected to the solenoid valve 14.

The solvent A and the solvent B are reserved in the reservoir 12 and the reservoir 13, respectively. The number of kinds of Solvents used is not limited to two. The number may be increased in accordance with intended purposes and applications. In general, a mixture of non-polar molecules and polar molecules is used as either the solvent A or the solvent B.

The solvent A and the solvent B are pumped by the pump 16 through the reservoir 15 and the solenoid valve 14 in a circuit of the liquid chromatograph 11. Under control signals from the liquid chromatograph control apparatus 21, the solenoid valve 14 chooses a solvent to be pumped between the solvent A and the solvent B. A mixture ratio of the solvent A and the solvent B contained in the mixer 15 is determined, depending on the time for choosing the individual solvents by the solenoid valve 14. The pumped solvents A and B are reserved in the mixer 15 for a while, to prepare eluent 10 therein. The eluent 10 prepared has a calculated mixture ratio, as mentioned later.

The injector 17 is designed to contain a sample 3 and inject it by allowing the eluent 10 to pass therethrough. The sample 3 is the same as the sample 3 of FIG. 1. The number of injectors 17 used is not limited to one. A plurality of injectors 17 may be arranged in parallel to form several route lines to be selectively chosen so that a plurality of samples can be continuously manipulated.

The column 18 is packed with a stationary phase. For liquid chromatography to be performed, the mixed solvent (eluent) 10 is forced to pass through the column 18. Silica gel forming the silica-gel thin-layered plate 2 of FIG. 1 is used as the stationary phase. The number of columns used is not limited to one. A plurality of columns 18 may be arranged in parallel to form several route lines to be selectively chosen so that plural types of liquid chromatography can be carried out.

The detector 19 detects the results of liquid chromatography performed on the column 18. The fraction collector 20 has a plurality of test tubes into which components included in the sample 3 are dispensed from one component to another with reference to the analysis of the detector 19.

Figure 4:
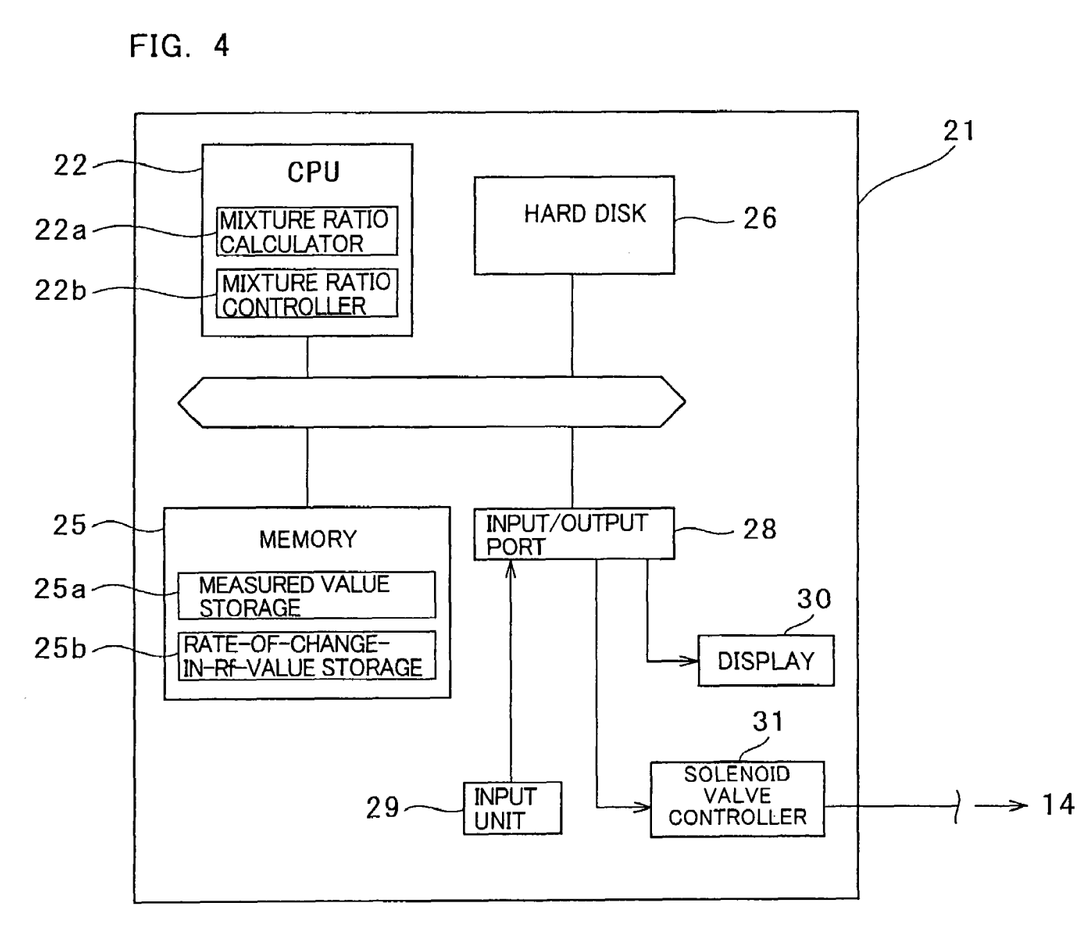
FIG. 4 is a block diagram of a liquid chromatograph control apparatus according to an embodiment of the present invention.

The liquid chromatograph control apparatus 21 is constituted by information processing equipment such as a general-purpose personal computer comprising, as shown in FIG. 4, a CPU 22 having a mixture ratio calculator 22a and a mixture ratio controller 22b; a memory 25 having a measured value storage 25a and a rate-of-change-in-Rf-value storage 25b; a hard disk 26; and an input/output port 28. The input/output port 28 is connected to an input unit 29 comprising e.g. a keyboard and a mouse, to a display 30 for presenting various information in the process of performing liquid chromatography to an operator, and to a solenoid valve controller 31 for sending open/close signals to the solenoid valve 14 under the instruction of the mixture ratio controller 22b of CPU 22.

A variety of software including a computer program for liquid chromatography according to one embodiment of the present invention is stored in the hard disk 26. The above-mentioned respective portions 22a, 22b, 25a, 25b are constructed by combination of the hardware and the software. The computer program can be installed in any computers by recording it in a removable recording media such as a CD-ROM (compact disk read-only memory) disk, a FD (flexible disk), and a MO (magnetooptic disk).

The measured value storage 25a stores measured retardation factor (Rf) values of the sample in association with a specified mixture ratio at which various ingredients are contained in eluent used for separation on thin layer chromatography. The data to be stored in the measured value storage 25a are the data obtained by performing thin layer chromatography in advance of liquid chromatography using the liquid chromatograph 11. The data may be entered through the input unit 29 by the operator.

The rate-of-change-in-Rf-value storage 25b stores a rate of change in the retardation factor (Rf) value of the sample with respect to variation in a mixture ratio of ingredients of eluent. The data stored in the rate-of-change-in-Rf-value storage 25b are the data previously obtained by performing thin layer chromatography using respective types of eluent different in combination of ingredients. The hard disk 26 stores a rate of change in the Rf value of the sample for respective types of eluent different in the combination of ingredients. When the computer program according to the embodiment is implemented, only the rate of change in the Rf value corresponding to eluent containing ingredients at the specified mixture ratio stored in the measured value storage 25a is loaded into the memory 25.

The mixture ratio calculator 22a calculates a mixture ratio of eluent at which a specified retardation factor value (RfO) is obtained, based on the measured Rf value corresponding to the specified mixture ratio stored in the measured value storage 25a and on the rate of change in the Rf value stored in the rate-of-change-in-Rf-value storage 25b. Detailed operation in the mixture ratio calculator 22a will be mentioned later.

Based on the calculated results by the mixture ratio calculator 22a, the mixture ratio controller 22b outputs control signals for controlling the mixture ratio of eluent fed into the column at which the Rf value of the sample becomes equivalent to the specified retardation factor value (RfO). The control signals are supplied to the solenoid valve controller 31 from the input/output port 28.

Figure 5:
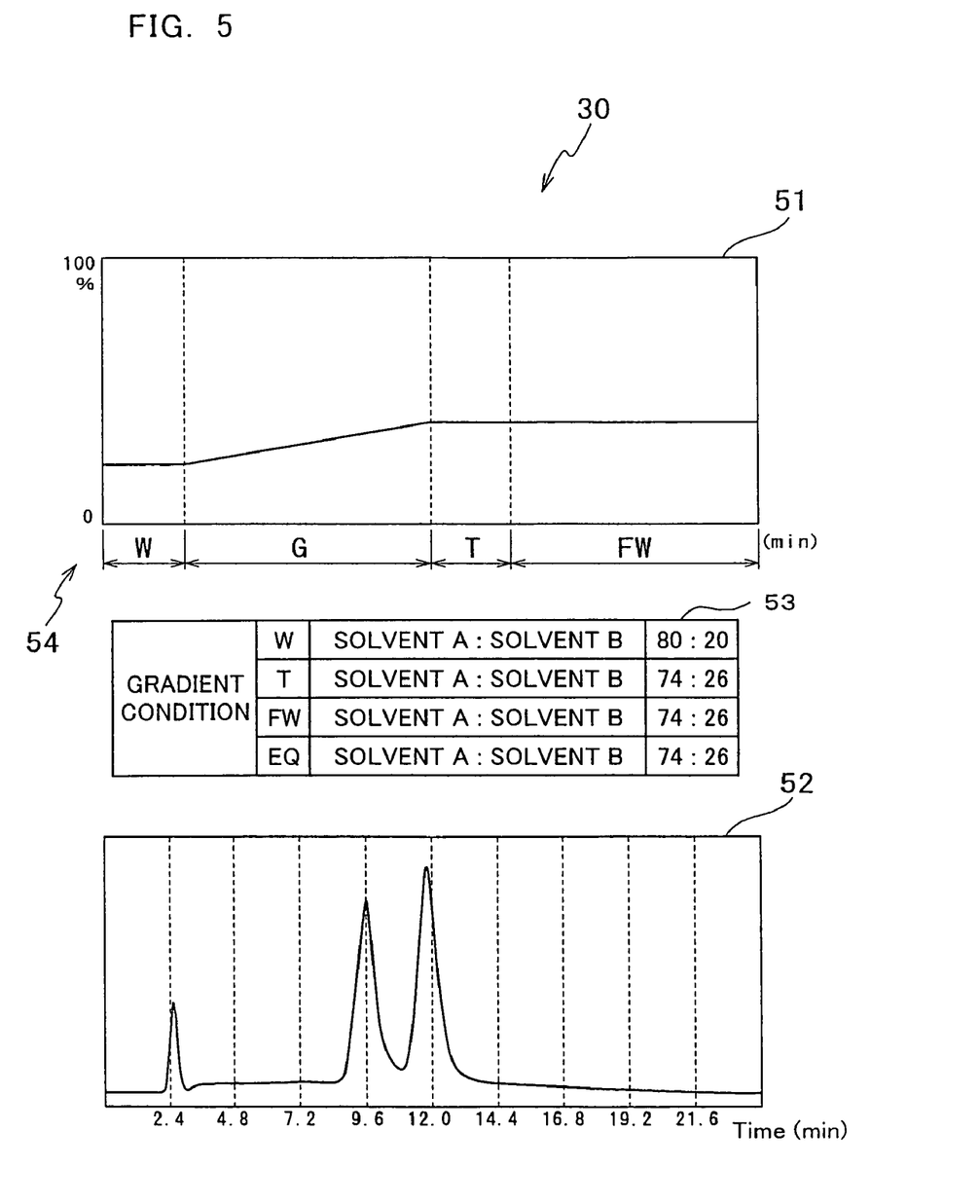
FIG. 5 is a diagram showing an example of representation displayed on a window of the liquid chromatograph control apparatus shown in FIG. 4.

As shown in FIG. 5, a graph 51, a graph 52 and a gradient condition table 53 are displayed on the display 30.

The graph 51 represents a time-rate-of-change in the mixture ratio (B/A+B) of the eluent 10 fed into the column 18 from the mixer 15, taking elapsed time as an axis of abscissas and a proportion of the solvent B contained in the eluent as an axis of ordinate. In the axis of abscissas, a time interval 54 is set for each of W (wait), G (gradient), T (top), FW (forward wash), and EQ (equilibration) arranged in this order. The graph 52 takes elapsed time as an axis of abscissas and absorbance as an axis of ordinate. The graph 52 represents an elution pattern of the sample 3, showing projection values of components contained in the sample 3 when the components are discharged from the column 18. The gradient condition table 53 shows a mixture ratio of the solvent A and the solvent B contained in the eluent 10 for each time interval. During the time interval G, the mixture ratio is gradually increased linearly up from that in W to that in T.

Next, an embodiment of a method for performing liquid chromatography of the present invention will be described.

(First step) First, a measured Rf value of the sample 3, which is obtained when using the eluent 4 containing the solvents A and B mixed at the specified mixture ratio, is obtained by the operator performing thin layer chromatography (TLC).

In TLC, the silica-gel thin layer 2 on which a droplet of the sample 3 is spotted as shown in FIG. 2(a) is dipped in the eluent 4, first, as shown in FIG. 1. Then, the mixed solution 4 is absorbed up into the silica-gel thin layer 2 by capillary action. Accordingly, the sample 3 is also moved up. After the end of movement of the eluent 4 and the sample 3, the sample 3 is moved to a location of sample 3', as shown in FIG. 2(b). Then, taking a distance between the position of the sample 3 before the silica-gel thin layer 2 is dipped in the mixed solution 4 and an upper end of the eluent 4 as 1.0, a distance between the position of sample 3' and the former position with respect to the distance of 1.0 is determined as the Rf value for sample 3.

(Second step) Following steps are taken place in the liquid chromatograph control apparatus 21. In the step S1 of FIG. 6, CPU 22 of the liquid chromatograph control apparatus 21 repeatedly makes a judgment on whether a measured Rf value obtained by TLC in the first step is input from the input unit 29 or not. After it is confirmed that the measured Rf value is input (S1: YES), the measured Rf value and the mixture ratio of the solvent A and solvent B contained in the mixed solution 4 at which the measured Rf value is obtained, i.e., the specified mixture ratio, are stored in the measured value storage 25a of the memory 25 in the step S2.

Figure 6:
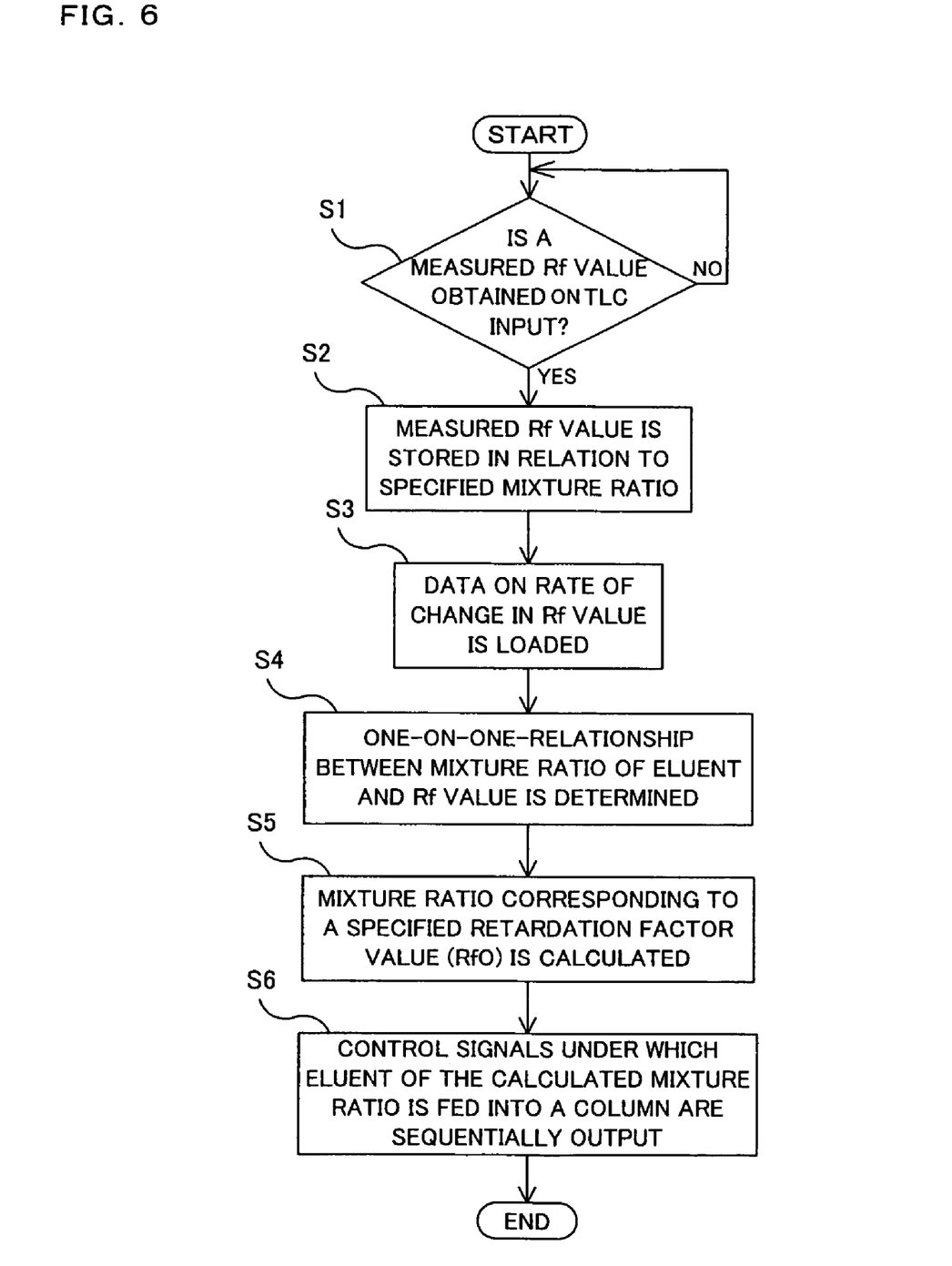
FIG. 6 is a flow chart of a method for performing liquid chromatography according to an embodiment of the present invention.

Then, in the step S3, the data on a rate of change in the Rf value of the sample with respect to variation in mixture ratio of ingredients of eluent that corresponds to the specified mixture ratio stored in the measured value storage 25a is read out from the hard disk 26 and loaded to the rate-of-change-in-Rf-value storage 25b.

Then, in the step S4, the mixture ratio calculator 22a determines one-on-one relationship between the mixture ratio of eluent and the Rf value based on a measured Rf value corresponding to the specified mixture ratio stored in the measured value storage 25a and on the rate of change in the Rf value stored in the rate-of-change-in-Rf-value storage 25b. As the data stored in the rate-of-change-in-Rf-value storage 25b is solely the data on the rate of change in the Rf value, the one-on-one relationship between the mixture ratio of eluent and the Rf value cannot be determined using the data in the rate-of-change-in-Rf-value storage 25b. Using the data, only the fact can be derived that a straight line representing the relation therebetween is any one of an infinite number of straight lines, such as straight lines 61, 62, 63, 64 (each having gradient that depends on the rate of change in the Rf value stored in the rate-of-change-in-Rf-value storage 25b) shown in the graph of FIG. 7 taking the mixture ratio as the axis of abscissas and the Rf value as the axis of ordinate. For this reason, through the use of a measured retardation factor value Rf1 corresponding to a specified mixture ratio X0 stored in the measured value storage 25a, a straight line passing through the coordinate (X0, Rf1) is selected from an infinite number of straight lines as an actual indication of the relation between the Rf value and the mixture ratio. For example, in the example shown in FIG. 7, the mixture ratio calculator 22a selects the straight line 63 as the indication of the relation therebetween.

Figure 7:
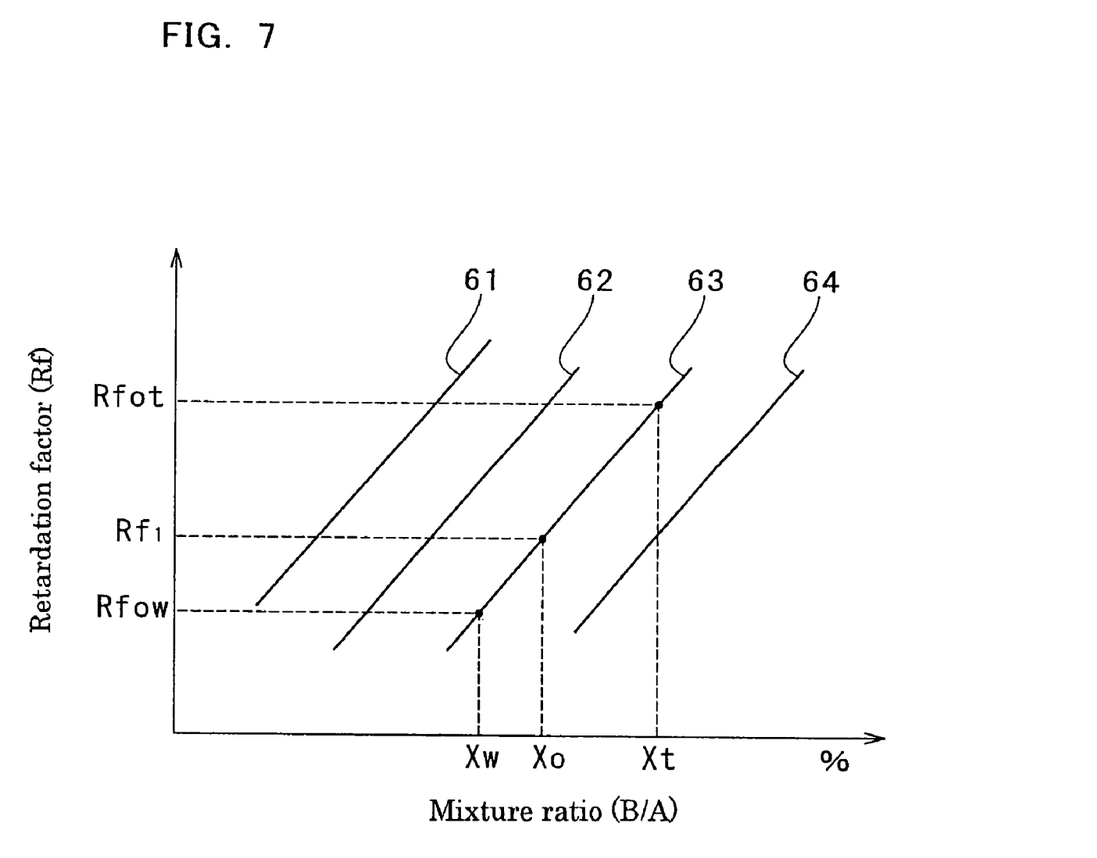
FIG. 7 is a graph taking a mixture ratio as an axis of abscissas and a retardation factor (Rf) value as an axis of ordinate.

In the step S5, the mixture ratio calculator 22a calculates the mixture ratio corresponding to the specified retardation factor value (RfO) required for the sample to be separated by the liquid chromatograph 11, based on the one-on-one relationship determined in the step S4. For example, when the gradient is processed as shown in the graph 51 of FIG. 5, the mixture ratio calculator 22a determines the mixture ratio values Xw, Xt respectively corresponding to the specified retardation factor values RfOw, RfOt during the time intervals "W" and "T", based on the straight line 63 as shown in FIG. 7. The mixture ratio thus determined is written on a given area in the memory 25, and shown on the display 30 as shown in the gradient condition table 53 of FIG. 5.

In the step S5, the time-rate-of-change in the mixture ratio of the eluent 10 shown in the graph 51 and the elution pattern of the sample 3 shown in the graph 52 may also be calculated.

Further explanation is given here regarding the calculation of the time-rate-of-change in the mixture ratio and the calculation of the elution pattern of the sample 3.

As aforementioned, the retardation factor value required for optimum separation is determined from the Rf value of the target component on TLC using the actual sample. This enables the necessary conditions for eluent required for optimum separation to be determined by a single TLC experimental test. Also, under the conditions for the eluent thus determined, retention time (tR) of the target component in the actual chromatography can also be determined from following equations:

$$Rf = 1/(k'+1)$$

$$k' = (tR - tO)/tO$$

where tO is retention time of non-retention component.

This can allow automatic determination on the total chromatography time required for the target component to be completely eluted. In the case of step elution or gradient elution, as requiring a shorter retention time (tR) than isocratic elution, the target component can be eluted within the total chromatograph time.

(Third step) In the step S6, the mixture ratio controller 22b sequentially outputs control signals to the solenoid valve controller 31 so that the eluent 10 having the mixture ratio determined in the step S5 can be fed into the column 18 for only a predetermined time. Under control of the control signals, the solenoid valve controller 31 outputs signals to the solenoid valve 14 to open and close the solenoid valve 14. This can allow the Rf value of the sample in the column 18 to be surely equivalent to the specified retardation factor value (RfO) or an approximation thereto, and as such can allow good separation of the sample.

Also, in the illustrated embodiment, since the rate of change in the Rf value of the sample with respect to variation in mixture ratio of ingredients of eluent is stored in the hard disk 26 for respective types of eluent different in combination of ingredients, only a required rate of change can be stored in the rate-of-change-in-Rf-value storage 25b. This enables the liquid chromatograph control apparatus 21 to be applied to a variety of eluent different in combination of ingredients.

Although there has been described certain preferred embodiments of the present invention, the present invention is not limited to the illustrated embodiments but various design changes and modifications may be made within the scope of the invention set forth in the annexed claims. For example, various modifications may be made to the concrete configuration of the liquid chromatograph 11. Also, the rate-of-change-in-Rf-value storage 25b may be constructed to store the rate of change in the Rf value of the sample with respect to variation in mixture ratio of ingredients of eluent for only one type of eluent. Also, the hardware construction of the liquid chromatograph control apparatus 21 may be changed arbitrarily.

Capability of Exploitation in Industry

According to the present invention, a mixture ratio of eluent for a desired retardation factor value (RfO) of a sample can be obtained by simply determining a Rf value of the sample for any specific mixture ratio of eluent in the thin layer chromatography. This enables chromatography to be preformed under such a condition of eluent as an optimum retardation factor value (RfO) is obtained, without troublesome works. Therefore, the workability in chromatography can be significantly improved.

The invention claimed is:

1. A liquid chromatograph control apparatus comprising:
    measured value storage that stores a measured retardation factor (Rf) value of a sample, which is obtained when components of the sample are separated on thin layer chromatography using eluent containing a plurality of ingredients at a specified mixture ratio, in association with the specified mixture ratio,
    rate-of-change-in-Rf-value storage that stores a rate of change in the retardation factor (Rf) value of the sample with respect to variation in mixture ratio of ingredients of eluent,
    mixture ratio calculator that determines a mixture ratio of the eluent at which a specified retardation factor value (RfO) of the sample is obtained, based on the measured retardation factor (Rf) value corresponding to the specified mixture ratio stored in the measured value storage and on the rate of change in the retardation factor (Rf) value stored in the rate-of-change-in-Rf-value storage, and
    mixture ratio controller that outputs a control signal to control the mixture ratio of the eluent fed into a column so that the retardation factor (Rf) value of the sample can be equivalent to the specified retardation factor value (RfO), based on calculated results by the mixture ratio calculator.

2. The liquid chromatograph control apparatus according to claim 1, wherein the rate-of-change-in-Rf-value storage can store a rate of change in the retardation factor (Rf) value of the sample with respect to variation in mixture ratio of ingredients of eluent, for respective types of eluent different in combination of ingredients.

3. A method for performing liquid chromatography comprising:
    a first step for obtaining a measured retardation factor (Rf) value of a sample by performing thin layer chromatography using eluent containing a plurality of ingredients at a specified mixture ratio,
    a second step for determining a mixture ratio of the eluent at which a specified retardation factor value (RfO) is obtained, by using a rate of change in the retardation factor (Rf) value of the sample with respect to variation in mixture ratio of the ingredients of the eluent, based on the measured retardation factor (Rf) value obtained in the first step and on the specified mixture ratio of the eluent at which the measured retardation factor (Rf) value is obtained, and
    a third step for feeding into a column the eluent having the mixture ratio determined in the second step at which the specified retardation factor value (RfO) is obtained.

4. A computer program for controlling a liquid chromatograph, wherein the program causes a computer to function as:
    measured value storage that stores a measured retardation factor (Rf) value of a sample, which is obtained when components of the sample are separated on thin layer chromatography using eluent containing a plurality of ingredients at a specified mixture ratio, in association with the specified mixture ratio,
    rate-of-change-in-Rf-value storage that stores a rate of change in the retardation factor (Rf) value of the sample with respect to variation in mixture ratio of the ingredients of the eluent,
    mixture ratio calculator that determines a mixture ratio of the eluent at which a specified retardation factor value (RfO) of the sample is obtained, based on the measured retardation factor (Rf) value corresponding to the specified mixture ratio stored in the measured value storage and on the rate of change in the retardation factor (Rf) value stored in the rate-of-change-in Rf-value storage, and mixture ratio controller that outputs a control signal to control a mixture ratio of eluent fed into a column so that the retardation factor (Rf) value of the sample can be equivalent to the specified retardation factor value (RfO), based on calculated results by the mixture ratio calculator.

* * * * *